(12) United States Patent
Silvis et al.

(10) Patent No.: US 9,194,274 B2
(45) Date of Patent: Nov. 24, 2015

(54) PARTICULATE MEASUREMENT SYSTEM

(75) Inventors: William Martin Silvis, Ann Arbor, MI (US); Roland Wanker, Hart bei Graz (AU)

(73) Assignee: AVL TEST SYSTEMS, INC., Plymouth, MI (US)

( * ) Notice: Subject to any disclaimer, the term of this patent is extended or adjusted under 35 U.S.C. 154(b) by 555 days.

(21) Appl. No.: 13/509,043

(22) PCT Filed: Aug. 6, 2010

(86) PCT No.: PCT/US2010/044633
§ 371 (c)(1),
(2), (4) Date: May 10, 2012

(87) PCT Pub. No.: WO2012/018344
PCT Pub. Date: Feb. 9, 2012

(65) Prior Publication Data
US 2012/0225488 A1  Sep. 6, 2012

(51) Int. Cl.
*F01N 11/00* (2006.01)
*F01N 3/035* (2006.01)

(52) U.S. Cl.
CPC .............. *F01N 11/007* (2013.01); *F01N 3/035* (2013.01); *F01N 2550/02* (2013.01); *F01N 2550/04* (2013.01); *Y02T 10/47* (2013.01); *Y10T 436/18* (2015.01); *Y10T 436/21* (2015.01)

(58) Field of Classification Search
CPC ..................................................... G01N 1/2252
USPC ...................................................... 73/114.71
See application file for complete search history.

(56) References Cited

U.S. PATENT DOCUMENTS

| | | | |
|---|---|---|---|
| 3,603,155 A | 9/1971 | Morris et al. | |
| 4,633,706 A | 1/1987 | Ito et al. | |
| 4,660,408 A | 4/1987 | Lewis | |
| 4,747,297 A | 5/1988 | Okayama et al. | |
| 4,916,384 A | 4/1990 | Ishida | |
| 5,072,416 A | 12/1991 | Francisco, Jr. et al. | |
| 5,100,632 A | 3/1992 | Dettling et al. | |
| 5,243,847 A | 9/1993 | Engeljehringer et al. | |
| 5,279,146 A * | 1/1994 | Asano et al. ................. | 73/28.04 |
| 5,431,042 A | 7/1995 | Lambert et al. | |
| 5,458,673 A | 10/1995 | Kojima et al. | |

(Continued)

FOREIGN PATENT DOCUMENTS

DE  40 05 803 A1  8/1990
DE  196 05 053 A1  9/1996

(Continued)

OTHER PUBLICATIONS

International Search Report for PCT Application No. PCT/US2010/044633, Oct. 1, 2010.

(Continued)

*Primary Examiner* — Hezron E Williams
*Assistant Examiner* — Mark A Shabman
(74) *Attorney, Agent, or Firm* — Harness, Dickey & Pierce, P.L.C.

(57) ABSTRACT

Disclosed is a vehicle emissions monitoring system capable of providing an accurate, real-time estimate of an amount of particulate matter (PM) within a vehicle's exhaust. The system is capable of accurately differentiating the composition of that PM by identifying amounts attributable to soot, SOF, and sulfate.

24 Claims, 3 Drawing Sheets

(56) References Cited

U.S. PATENT DOCUMENTS

| | | | |
|---|---|---|---|
| 5,474,745 A | 12/1995 | Fukui et al. | |
| 5,941,918 A | 8/1999 | Blosser | |
| 6,148,656 A | 11/2000 | Breton | |
| 6,151,952 A | 11/2000 | Mathews et al. | |
| 6,308,130 B1 | 10/2001 | Vojtisek-Lom | |
| 6,370,936 B1 | 4/2002 | Yamagishi et al. | |
| 6,382,014 B1 | 5/2002 | Breton | |
| 6,435,019 B1 | 8/2002 | Vojtisek-Lom | |
| 6,470,732 B1 | 10/2002 | Breton | |
| 6,516,654 B2 | 2/2003 | Uchihara et al. | |
| 6,615,678 B2 | 9/2003 | Yamagishi et al. | |
| 6,727,097 B2 | 4/2004 | Kumar et al. | |
| 6,785,605 B2 | 8/2004 | Huller et al. | |
| 6,796,165 B2 | 9/2004 | Abdul-Khalek | |
| 6,857,327 B2 | 2/2005 | Silvis et al. | |
| 6,865,472 B2 | 3/2005 | Nakamura | |
| 6,959,590 B2 | 11/2005 | Hendren et al. | |
| 6,973,818 B2 | 12/2005 | Silvis et al. | |
| 7,000,449 B2 | 2/2006 | Silvis et al. | |
| 7,055,364 B2 | 6/2006 | Silvis et al. | |
| 7,299,690 B2 | 11/2007 | Graze, Jr. | |
| 7,328,606 B2 | 2/2008 | Nakamura | |
| 7,389,703 B2 | 6/2008 | Wei et al. | |
| 7,434,449 B2 | 10/2008 | Kusaka et al. | |
| 7,454,950 B2 | 11/2008 | Nakamura | |
| 7,474,953 B2 | 1/2009 | Hulser et al. | |
| 2002/0173919 A1 | 11/2002 | Moteki et al. | |
| 2003/0049191 A1 | 3/2003 | Twigg | |
| 2003/0131586 A1 | 7/2003 | Kato et al. | |
| 2004/0040287 A1 | 3/2004 | Beutel et al. | |
| 2004/0064243 A1 | 4/2004 | Nakamura | |
| 2004/0139785 A1* | 7/2004 | Abdul-Khalek | 73/28.01 |
| 2004/0193358 A1 | 9/2004 | Yasui | |
| 2005/0138917 A1 | 6/2005 | Maki | |
| 2006/0144124 A1 | 7/2006 | Kusaka et al. | |
| 2006/0234514 A1 | 10/2006 | Gianoulakis et al. | |
| 2006/0236752 A1 | 10/2006 | Nakamura | |
| 2007/0006577 A1 | 1/2007 | Yokoyama et al. | |
| 2007/0056272 A1 | 3/2007 | Dollmeyer et al. | |
| 2008/0120963 A1 | 5/2008 | Morita et al. | |
| 2009/0003125 A1 | 1/2009 | Kusaka et al. | |
| 2009/0064758 A1* | 3/2009 | Walter et al. | 73/23.31 |
| 2009/0266040 A1 | 10/2009 | Schramm et al. | |
| 2010/0018850 A1 | 1/2010 | Adhvaryu et al. | |
| 2010/0043527 A1 | 2/2010 | Marra | |

FOREIGN PATENT DOCUMENTS

| | | |
|---|---|---|
| EP | 0 092 023 A1 | 10/1983 |
| EP | 0 319 299 A2 | 6/1989 |
| EP | 1 914 536 A1 | 4/2008 |
| WO | 91 05241 A1 | 4/1991 |

OTHER PUBLICATIONS

C. Arcourmanis and A. Megaritis: Real-Time Measurement of Particulate Emissions in a Turbocharged DI Diesel Engine, SAE International, SAE Technical Paper Series 922390, International Fuels and Lubricants Meeting and Exposition, San Francisco, California, Oct. 19-22, 1992.

Justin M. Kern: Inventory and Prediction of Heavy-Duty Diesel Vehicle Emissions, A Thesis Submitted to The College of Engineering and Mineral Resources at West Virginia University, Morgantown, West Virginia, 2000.

Nigel N. Clark, Ronald P. Jarrett & Christopher M. Atkinson (1999): Field Measurements of Particulate Matter Emissions, Carbon Monoxide, and Exhaust Opacity from Heavy-Duty Diesel Vehicles, Journal of the Air & Waste Management Association, 49:9, 76-84.

* cited by examiner

PARTICULATE MEASUREMENT SYSTEM

BACKGROUND

This disclosure relates to a system for monitoring the amount (mass, weight, concentration, etc.) of particulate matter (PM) within a vehicle's exhaust, or emissions. The system may be utilized on-board a vehicle to provide an accurate, differentiated PM measurement.

PM refers, generally, to matter suspended in a fluid (e.g., a gas) in the form of very small particles or droplets. The term exhaust (or, aerosol, exhaust gas, exhaust sample, etc.), refers to a fluid and the PM carried therein. PM is commonly emitted from engines and typically includes carbonaceous matter in elemental form (or, soot) and carbonaceous matter in the form of volatile and semi-volatile hydrocarbon compounds (which may be SOF, or soluble organic fraction), and other organic and inorganic compounds (such as sulfates).

Certain vehicles may be required to emit PM at a level below a predetermined threshold during government mandated emissions test procedures, including so called not-to-exceed measurement events (NTE events), or during normal use. The amount of PM expelled by such a vehicle under test is indicative of engine efficiency, fuel quality, vehicle pollution, etc. PM within exhaust can be collected by, or can stick to, a measurement filter through which the exhaust passes. In one known type of test, PM is monitored utilizing a measurement filter that collects substantially all PM within a sample of the vehicle's exhaust. The measurement filter is removed from the sampling apparatus and the amount of PM collected by the filter is determined in a laboratory, for example.

SUMMARY

Disclosed is a system having a sensor, a filter and a computer. The computer includes a processor, and is programmed to identify at least one quantity within an exhaust sample based on at least one parameter associated with another exhaust sample. The at least one quantity within the exhaust sample can be, for example, the amount (e.g., quantity, mass, weight, concentration, etc.) of soot, SOF, and/or sulfate within the exhaust sample. Further, the at least one parameter can be, for example, a SOF to soot proportionality factor associated with the other exhaust sample, and/or a sulfate-make factor associated with the other exhaust sample.

Further disclosed is a method including the steps of providing an exhaust sample for a time period, and identifying a quantity corresponding to a portion of a total amount of PM within the exhaust sample. This quantity can be identified based at least in part on an identified parameter, which may be a parameter (e.g., factor, value, quantity, etc.) associated with another exhaust sample.

These and other features of the present disclosure can be best understood from the following specification and drawings, the following of which is a brief description.

BRIEF DESCRIPTION OF THE DRAWINGS

The drawings that accompany the following detailed description can be briefly described as follows.

DETAILED DESCRIPTION

Figure 1:
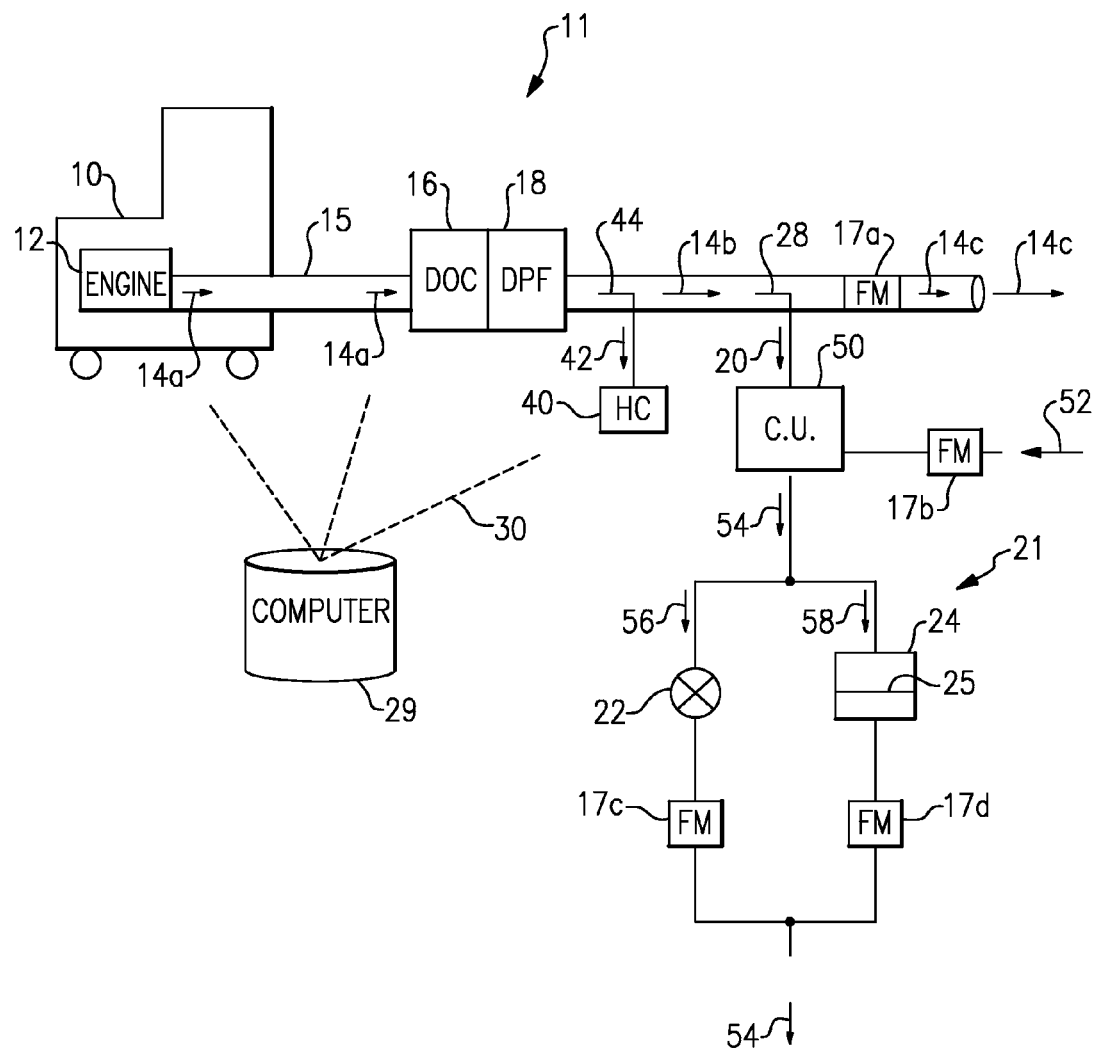
FIG. 1 shows a PM monitoring system arranged with the exhaust system of an engine.

Referring to FIG. 1, a PM monitoring system 21 is arranged with an exhaust system 11 of a vehicle 10. The engine 12 of the vehicle 10 generates exhaust 14a, which flows from the engine 12, downstream to the atmosphere. The exhaust 14a is routed away from the engine 12 by way of exhaust piping 15. The engine 12 may be a diesel engine, for example, and the exhaust system 11 may include a diesel oxidation catalyst (DOC) 16 and a diesel particulate filter (DPF) 18 arranged in-line with the exhaust piping 15. As shown, a flowmeter 17a is arranged downstream of the DOC 16 and the DPF 18, however flowmeters may also be arranged upstream of the DOC 16 and the DPF 18.

Downstream of the DOC 16 and the DPF 18 are exhaust samplers 44 and 28. Sampler 44 directs a sample 42 (e.g., a sample exhaust flow) of exhaust 14a to a total hydrocarbon (THC, or total HC) analyzer unit 40, which may be heated, configured to identify the THC gas concentration present within the sample 42. In this regard, the THC analyzer unit 40 may be any type of known THC analyzer. Further, sampler 28 directs a sample 20 of exhaust 14b to a conditioning unit 50 upstream of a sensor 22 and a measurement filter unit 24. Exhaust 14b is defined as exhaust 14a less sample 42, and exhaust 14c is defined as exhaust 14b less exhaust sample 20, however, since the samples 20, 42 are small, the properties and flow rates of the exhaust 14b-c are substantially similar to 14a.

The conditioning unit 50 essentially acts to dilute the exhaust sample 20, and to provide a diluted exhaust flow 54 to the sensor 22 and the measurement filter unit 24. In particular, the conditioning unit combines a diluent 52, which may be air or another appropriate diluting fluid, with the exhaust sample 20. The flow rate of the diluent 52 may be monitored with a flowmeter 17b. The flow rate of the diluent 52 may be used to identify the amount of diluent 52 contained in the diluted exhaust flow 54. As will be explained below, it may be useful to determine the amount of dilution taking place in the conditioning unit 50 for the purposes of determining flow rates and various concentrations, for example. For reference, the diluted exhaust flow 54 will be referred to as the diluted sensor flow 56 and the diluted filter flow 58.

The sensor 22 and the measurement filter unit 24 are arranged in parallel such that they receive their respective diluted exhaust flows 56, 58. The flow rate of the diluted sensor and filter flows 56, 58 may be measured by flowmeters 17c, 17d positioned downstream of the sensor 22 and the measurement filter unit 24, respectively. Additional flowmeters may be included in-line with the exhaust system 11, or in-line with the PM monitoring system 21, as desired. The flowmeters 17a-d may be critical flow venturis, or thermal mass flow meters, for example.

The sensor 22 may be the AVL 483 Micro Soot Sensor (MSS), for example. In any case, the sensor 22 is configured to measure a concentration of soot within the diluted sensor flow 56 (or any exhaust sample), and the sensor 22 outputs this measured concentration as a function of time. The measurement filter unit 24 includes a measurement filter 25 that is capable of collecting substantially all of the PM within the diluted filter flow 58. The measurement filter unit 24 may be a type of gravimetric filter, or any other appropriate type of filter unit.

A computer 29, may be onboard the vehicle 10 and may receive information from various devices, such as temperature sensors and flowmeters 17a-d, that are associated with various parameters of the engine 12, the exhaust system 11, and the PM monitoring system 21. The computer 29 may communicate with these various devices by way of electrical harnesses 30, for example. In particular, the computer 29 receives at least the following information in real-time: the temperature of the exhaust gas (which, for example, may be reported to the computer 29 by a temperature sensor proximate the flowmeter 17a; the temperature of the exhaust gas 14c proximate the flowmeter 17a is substantially similar to the temperature of the exhaust 14a at, or in, the DOC 16); the flow rate of the exhaust 14a-c, the diluted exhaust flow 54 and the diluent 52 (as reported by the respective flowmeters 17a-d); the concentration of the soot within the diluted sensor flow 56 (as reported by the sensor 22), etc. The computer 29 and the electrical harnesses 30 may be arranged to receive other relevant information from the engine 12, exhaust system 11, and PM monitoring system 21 as needed. Temperature sensors and the like may be arranged on the engine 10, exhaust system 11, and the PM monitoring system 21 (and in other locations as needed) using known methods.

The computer 29 may store information (in memory, such as RAM, or on a hard drive, etc.) and may include one or more, integral or separate, processors programmed to perform various algorithms, functions, etc. The computer 29 may further include a monitor, and the computer 29 may be configured to display useful information on the monitor.

As explained above, known PM monitoring systems are generally concerned with an undifferentiated, total amount of PM. However, as elemental sulfur (S) may be present in fuel and lubrication oil, droplets of sulfate may become present on the measurement filter 25. Sulfate may be formed as a result of the combustion of elemental sulfur (S) within the engine 12, which oxidizes the elemental sulfur (S) and under certain conditions forms gaseous sulfate ($SO_3$). This gaseous sulfate may combine with water and form sulfuric acid ($H_2SO_4$). This sulfate formation is largely dependent on the presence and temperature of the exhaust gasses in the DOC 16 (e.g., $Temp_{DOC}$). For example, if a DOC 16 is not present, little $H_2SO_4$ will form. Additionally, if the DOC 16 is present, as shown in FIG. 1, substantial $H_2SO_4$ will only form if the DOC is sufficiently hot (e.g., if $Temp_{DOC}$ is at or above an activation temperature). If formed, this sulfuric acid, $H_2SO_4$, may further nucleate and cool, creating nanoparticles of sulfate which may be collected by, or may "stick" to, the measurement filter 25, or it may adsorb to the soot particles. Because this sulfate can become present on the measurement filter 25, it will be considered PM.

Similarly, some amount of the semi-volatile hydrocarbons present in the exhaust 14a-c may adsorb to the soot particles in the exhaust 14a-c as the exhaust 14a-c is sampled and cooled. Thereby, this amount of semi-volatile hydrocarbons will become the so-called SOF portion of the total PM (or, the amount of PM attributable to SOF). SOF formation depends on the amount of such HC gasses in the hot exhaust 14a-c (as measured by the THC analyzer unit 40), the temperature of the cooled sample (e.g., sample 20, which is typically 47° C.), reaction time, and other chemical and surface properties of the materials. This SOF portion can be characterized by the portion of the available semi-volatile HC gasses that react with the available soot particles under the prevailing operating conditions (including pressures and temperatures). A practical determination of this proportionality is described below.

In order to better understand the composition of the PM within a given sample of exhaust, the amount of sulfate within that sample of exhaust should be accurately estimated. By estimating the amount of sulfate within a sample of exhaust, one can understand the composition of the PM within a vehicle's exhaust, and thus one can study the relationship of that exhaust to vehicle pollution, engine performance, after treatment efficiency, effect on human health and the environment, etc.

The example exhaust system 11 and the method (represented in FIGS. 2-3) accounts for sulfates and SOF within exhaust to in order provide an accurate, differentiated measurement of the composition of the PM within that exhaust (e.g., by accounting for the separate portions of the total PM attributable to soot, SOF, and sulfate).

Figure 2:
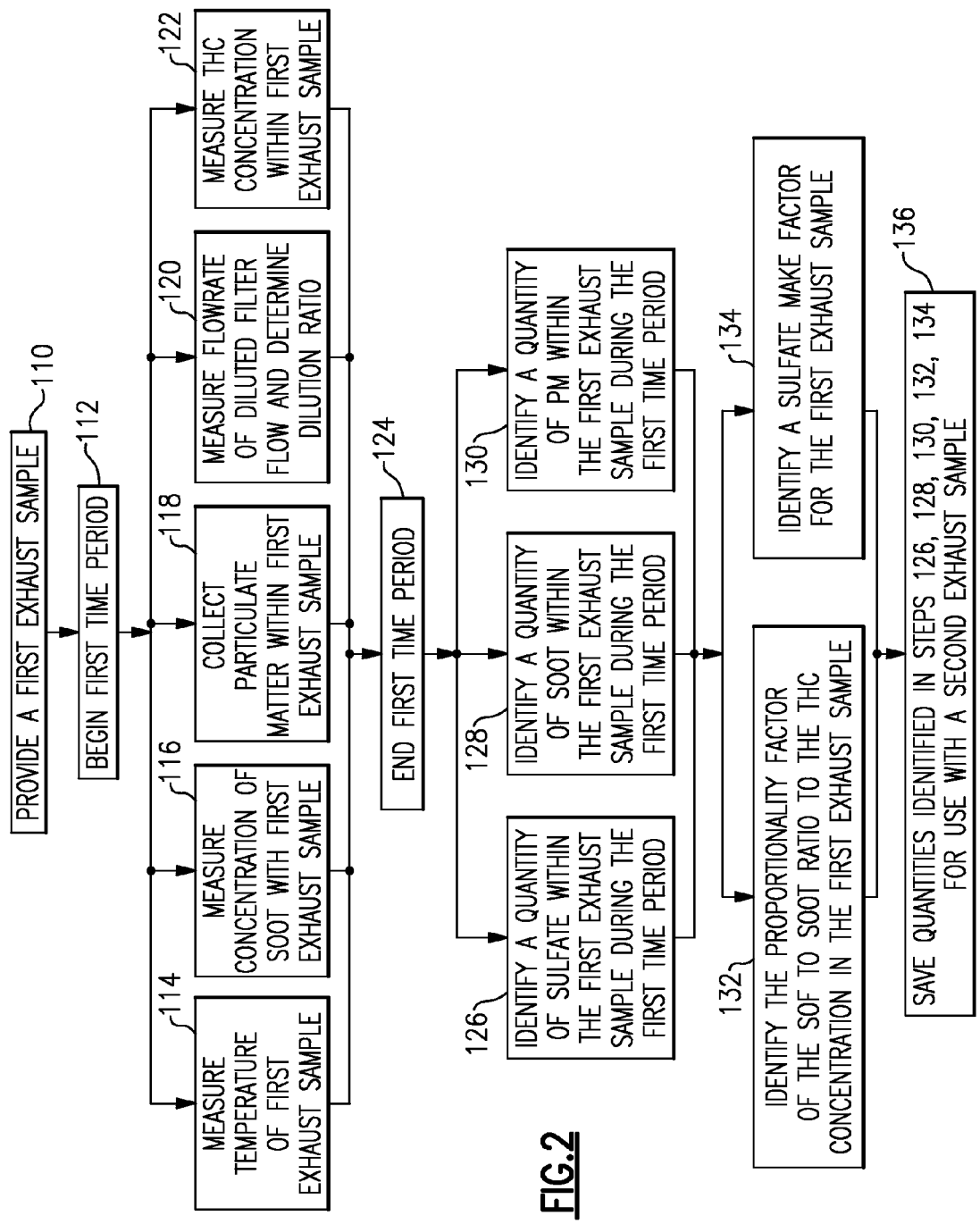
FIG. 2 is a flow chart representative of the steps for identifying quantities corresponding to soot, sulfate, and SOF within a first exhaust sample, and for determining parameters associated with the first exhaust sample.

FIG. 2 shows a flowchart representative of the steps for identifying the composition of the PM within a first sample of exhaust. The first exhaust sample (and the second exhaust sample, referred to in FIG. 3) may be provided in a manner similar to how the exhaust 14a-c, including the samples 20, 42, is shown in FIG. 1. The first exhaust sample is provided, at step 110, for a first time period ($T_1$), which is the time between steps 112 and 124.

During the first time period ($T_1$), the temperature of the exhaust sample 20 is monitored at step 114. Specifically, it may be useful to monitor the temperature of the diluted filter flow 58 ($Temp_{1-ex-filter}$) at step 114, by way of a temperature senor associated with the measurement filter unit 24. At step 116, the sensor 22 measures the concentration of soot ($C_{1-soot}(t)$) within the diluted sensor flow 56 as a function of time and communicates that measurement to the computer 29. Meanwhile, the filter 25 of the measurement filter unit 24 collects substantially all the PM within the diluted filter flow 58, represented at step 118, and the flow rate of the diluted filter flow 58 ($q_{1-ex-filter}$) is monitored by the flowmeter 17d located downstream of the measurement filter unit 24, as indicated at step 120. Additionally, at step 122, the THC concentration of the exhaust sample 42 is determined, as a function of time, by the THC analyzer unit 40 ($HC_1(t)$). All data is then transmitted to the computer 29 and stored therein.

Notably, the flow rate of the diluted filter flow 58 may provide similar accuracy in this respect to, say, the flow rate of the diluted sensor flow 56, since many of the quantities identified in the method shown in FIG. 2 are associated with the measurement filter unit 24. Further, the flow rate ($q_{1-ex-filter}$) used in the below formulae may be the measured flow rate of the diluted filter flow 58. The amount that the sample has been diluted can be determined from a dilution ratio which relates the flow rate of the diluted exhaust flow 54 to the flow rate of the diluent 52.

In a lab, for example, a quantity corresponding to the amount of sulfate ($M_{1-sulfate}$) collected by the filter 25 during the first time period can be identified, as represented at 126. Step 126 may be performed using known methods, such as ion exchange chromatography. The filter 25 can be further analyzed and a quantity corresponding to the total amount (mass, weight, etc.) of PM ($M_{1-PM}$) collected by the filter 25 during the first time period can be identified, represented at step 130. In particular, step 130 may be performed by comparing the weight, or mass, of the filter 25 before the first time period to the weight/mass of the filter 25 after the first time period.

Utilizing the concentration of soot within the first exhaust sample ($C_{1-soot}(t)$) as derived from the sensor 22, the flow rate through the measurement filter 25 ($q_{1-ex-filter}$), and the time period ($T_1$), the amount of soot ($M_{1-soot}$) within the first exhaust sample may be determined (using the computer 29, or another, separate computer, if post-processing is used) in the following manner, represented at step 128.

$$M_{1\text{-}soot} = \left( \int_{T_1} C_{1\text{-}soot}(t) \cdot q_{1\text{-}ex\text{-}filter} \cdot dt \right)$$

Utilizing the above identified quantities, an amount (mass, weight, etc.) of SOF ($M_{1\text{-}SOF}$) within the first exhaust sample during the first time period can be identified. For example, the amount of SOF ($M_{1\text{-}SOF}$) can be identified by subtracting $M_{1\text{-}sulfate}$ and $M_{1\text{-}soot}$ from $M_{1\text{-}PM}$.

$$M_{1\text{-}SOF} = M_{1\text{-}PM} - M_{1\text{-}soot} - M_{1\text{-}sulfate}$$

At step 132, a proportionality factor ($\alpha$) associated with the first exhaust sample is identified. For example, a SOF to soot ratio in the first exhaust sample depends on the presence of a portion (e.g., the portion that may ultimately adsorb to the soot particles) of the available semi-volatile HC gasses in the first exhaust sample, which may be represented by a proportionality factor ($\alpha$). The proportionality factor ($\alpha$) is generally represented as follows (where $C_{SOF}$ is the concentration of SOF within an exhaust sample, $C_{soot}$ is the concentration of soot within that exhaust sample, and HC is the total hydrocarbon gas concentration within that exhaust sample).

$$\frac{C_{SOF}}{C_{soot}} = \alpha \cdot HC$$

For example, a portion of the available semi-volatile HC within the exhaust 14a-c may adsorb to the soot present in the diluted filter flow 58. In this sense, the adsorbed semi-volatile HC has effectively become SOF. That is, since the adsorbed semi-volatile HC would be collected by the filter 25, it would be PM, and thus it would define an SOF portion of the PM. The sensor 22, on its own, cannot account for SOF, because the sensor 22 only measures the concentration of soot in a given exhaust sample. Accordingly, the THC concentration ($HC_1(t)$) measured by the THC analyzer unit 40, and adjusted for dilution at the conditioning unit 50, represented at step 122, is used to calculate the proportionality factor ($\alpha$) as follows.

$$\alpha = \frac{M_{1\text{-}SOF}}{\int_{T_1} C_{1\text{-}soot}(t) \cdot HC_1(t) \cdot q_{1\text{-}ex\text{-}filter}(t) \cdot dt}$$

This above-defined value $\alpha$ is representative of a ratio of SOF to soot in the first exhaust sample, as the ratio relates to a measured hydrocarbon gas concentration (with adjustment for dilution of the sample), and can be used to accurately predict the amount of SOF within any other exhaust sample without the need to analyze a filter 25 in a lab.

As explained above, the amount of sulfate within the first exhaust sample can be determined in a lab for the first exhaust sample, for which the filter measurement is available. However, the amount of sulfate within other exhaust samples and/or during other time periods is determined by other means. Accordingly, a sulfate-make factor (K) is identified at step 134, and can used to identify, or predict, the amount of sulfate within other exhaust samples.

In particular, the amount of sulfate within a sample of exhaust can depend on several factors, which may include: the amount the sulfur (S) within the fuel ($S_{fuel}$), the flow rate of the fuel ($\dot{m}_{fuel}$), temperature of the exhaust sample, temperature in the DOC 16 ($Temp_{DOC}$), flow rate of the exhaust, etc. Other factors may be important, and can be incorporated as appropriate.

With specific reference to step 134, the sulfate-make factor (K) is identified, with respect to the first exhaust sample, based on the known amount of sulfate ($M_{1\text{-}sulfate}$), the flow rate of the diluted filter flow 58 ($q_{1\text{-}ex\text{-}filter}$), and the time of the first time period ($T_1$).

$$M_{1\text{-}sulfate} = \int_{T_1} C_{1\text{-}sulfate} \cdot q_{1\text{-}ex\text{-}filter} \cdot dt$$

In the above equation, $C_{1\text{-}sulfate}$, is a calculated sulfate concentration within a given sample of exhaust (e.g., determined using the quantities identified in steps 120 and 126), in this case the first exhaust sample. With other exhaust samples and/or during other time periods, this concentration is determined based, in part, on a prediction from a computer based sulfate-concentration-model (e.g., based in the computer 29), and on a sulfate-make factor (K). The sulfate-concentration-model accounts for factors known to correlate to sulfate concentration. For example, as explained above, the amount of sulfate in a given sample of exhaust is proportional to the amount of sulfur (S) within the fuel ($S_{fuel}$), the flow rate of fuel (e.g., $\dot{m}_{fuel}$, or the rate of fuel consumed by the engine 10), the temperature of the exhaust 14a in the DOC 16 ($Temp_{1\text{-}ex}$) (which may be represented by the temperature of the exhaust 14c, as determined by a temperature sensor proximate the flowmeter 17a), and the flow rate of exhaust through (or, in) the DOC 16 ($q_{1\text{-}ex}$) (which may be the flow rate of the exhaust 14c, as determined by flowmeter 17a). $C_{1\text{-}sulfate}$ can be represented as follows.

$$C_{1\text{-}sulfate} = K(S_{fuel}, \dot{m}_{fuel}, Temp_{1\text{-}ex}, q_{1\text{-}ex})$$

Given at least the inputs $S_{fuel}$, $\dot{m}_{fuel}$, $Temp_{1\text{-}ex}$, and $q_{1\text{-}ex}$, the computer based sulfate-concentration-model predicts a sulfate concentration. Then, given the above calculated $C_{1\text{-}sulfate}$ and $M_{1\text{-}sulfate}$, the sulfate-make factor (K) can be determined. This value K, coupled with the pre-existing computer based sulfate-concentration-model, can be used to accurately predict the amount of sulfate within any exhaust sample.

The quantities (e.g., values, parameters, etc) identified in the above-identified steps may be saved on the computer 29 for use with another exhaust sample, indicated at step 136. Of particular interest, however, are the parameters sulfate-make factor (K) and the proportionality factor ($\alpha$). The quantities needed to determine these parameters (e.g., $M_{1\text{-}PM}$ and $M_{1\text{-}sulfate}$) may be input into the computer 29 by way of a user input field associated with the computer 29. The computer 29 can then access and use these quantities as needed.

Figure 3:
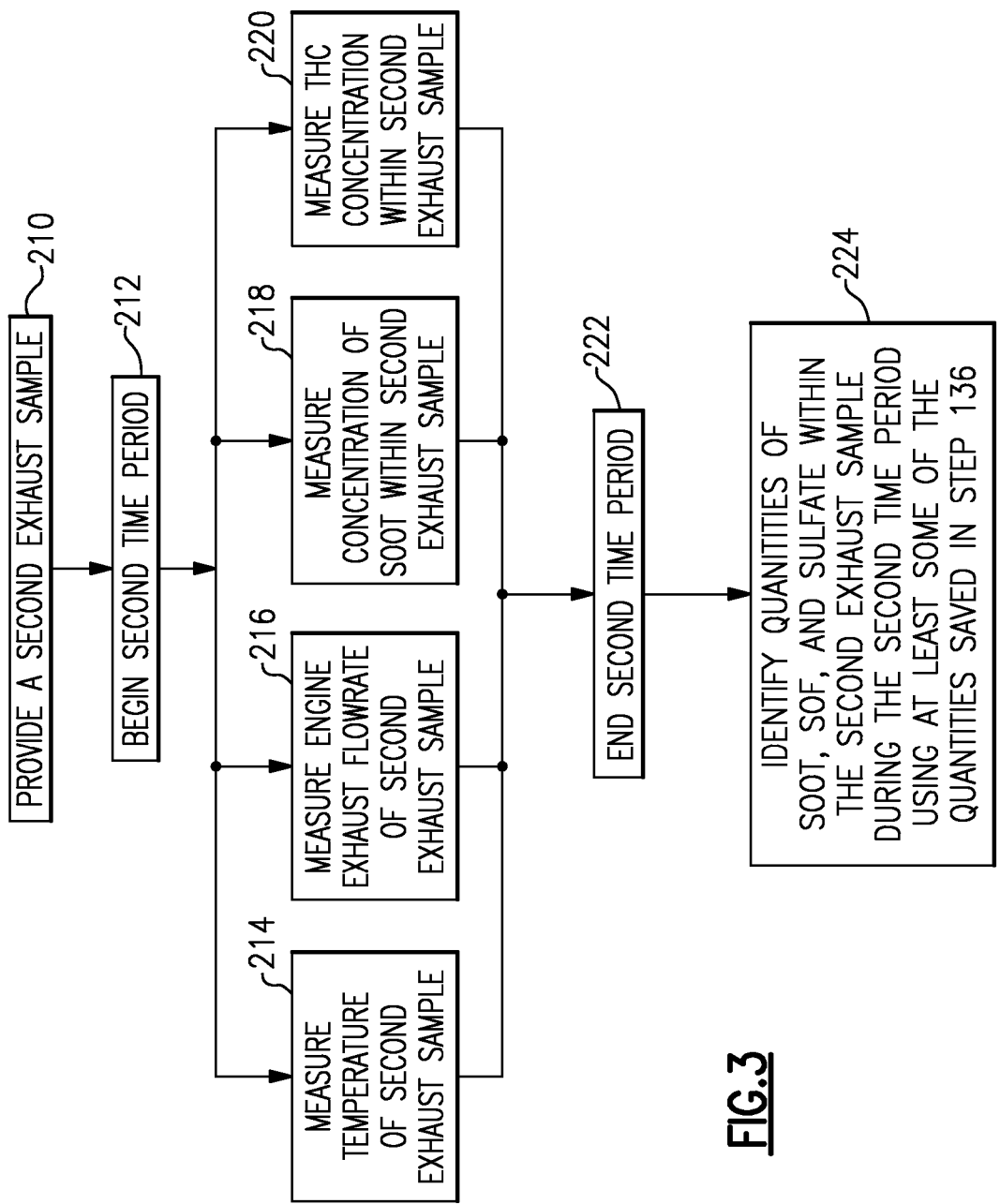
FIG. 3 is a flow chart representative of the steps for identifying quantities corresponding to soot, sulfate, and SOF within a second exhaust sample based on at least some of the parameters/quantities identified in the first exhaust sample.

Referring to FIG. 3, a second exhaust sample is provided, as represented at step 210, and the amount of PM, and the composition of that PM, within the second exhaust sample can be accurately determined. In the example shown, the second exhaust sample is provided during an NTE event, which defines the second time period (represented as the time between steps 212 and 222).

Notably, the second exhaust sample may exist during first exhaust sample. That is, the first exhaust sample may be taken during the course of an eight-hour driving day, and the vehicle may experience an NTE even for only a small portion of that day. In such a case, the first exhaust sample would include the second exhaust sample, but due to post-processing and storage of data in real-time, the quantities identified in the first exhaust sample can be used to determine the composition of the PM in the second sample. There may even be several second samples taken during the first sample. In some instances there may not be any second samples during the first sample (e.g., the first sample may be taken during an eight hour driving day, and no NTE events occur during that day). In that instance, the quantities identified in the first sample (e.g., K, α) may still be used in the second sample, whenever it occurs (e.g., the first and second sample can occur in sequence or on different days).

During the second time period ($T_2$) (which, again, may be an NTE event), the temperature of the second exhaust sample ($Temp_{2-ex}$) is measured at step 214. This temperature, $Temp_{2-ex}$, is indicative of the temperature of the exhaust 14a-c in the exhaust piping 15 and the DOC 16. Accordingly, a temperature sensor is associated with the exhaust piping 15 near the associated flowmeter 17a shown in FIG. 1, for example.

The flow rate of the second exhaust sample is also measured during this second time period, at step 216. The flow rate of particular interest during the second time period is the flow rate of the exhaust 14c in the exhaust piping 15 ($q_{2-ex}$). Further, the second exhaust sample is routed to the sensor 22. In step 218, the sensor 22 continuously measures the concentration of soot within the second exhaust sample as a function of time ($C_{2-soot}(t)$) and communicates the measurement to the computer 29. Concurrently, at step 220, the concentration of THC within the second exhaust sample is measured by the THC analyzer unit 40. From this, the HC concentration, $HC_2(t)$, that would be present in the gasses sampled by a measurement filter arranged to measure PM by known required sampling procedures, if such a filter were present, is determined.

Next, at step 224, quantities corresponding to amounts of SOF, soot, and sulfate within the second exhaust sample are identified. First, an amount of soot within the second exhaust sample ($M_{2-soot}$) can be identified. This may be performed by the computer 29, given the soot concentration measurement from the sensor 22 ($C_{2-soot}(t)$) taken at step 218, with known adjustments and calibrations, and given the flow rate of the exhaust during the second sample period ($q_{2-ex}$) and the second time period ($T_2$), as follows.

$$M_{2-soot} = \left( \int_{T_2} C_{2-soot}(t) \cdot q_{2-ex} \cdot dt \right)$$

Consistent with the above, the amount of PM within the second exhaust sample ($M_{2-PM}$) may be defined as the combination of soot ($M_{2-soot}$), SOF ($M_{2-SOF}$), and sulfate ($M_{2-sulfate}$). Notably, the SOF to soot proportionality factor (α) identified in step 132 may be used to identify the amount of SOF in the second exhaust sample as follows.

$$M_{2-SOF} = \int_{T_2} C_{2-soot}(t) \cdot \alpha \cdot HC_2(t) \cdot q_{2-ex} \cdot dt$$

Further, and given $S_{fuel}$, $\dot{m}_{fuel}$, $q_{2-ex}$, and $Temp_{2-ex}$, the computer based sulfate-concentration-model and the sulfate-make factor (K) identified in step 134 may be used, together with adjustments for the amount of dilution that would be performed in laboratory sampling (e.g., dilution_adjustment), to predict the concentration of sulfate in the second exhaust sample ($C_{2-sulfate-predict}$). For example:

$$C_{2-sulfate-predict} = K \cdot (S_{fuel}, \dot{m}_{fuel}, Temp_{2-ex}, q_{2-ex}) \cdot (\text{dilution\_adjustment})$$

This predicted concentration, $C_{2-sulfate-predict}$, can then be used to determine the amount of sulfate within the second exhaust sample as follows.

$$M_{2-sulfate} = \int_{T_2} C_{2-sulfate-predict} \cdot q_{2-ex} \cdot dt$$

Accordingly, using the above equations/algorithms, differentiated portions of the PM present in the second exhaust sample can be identified (e.g., masses of soot, SOF, and sulfate can be identified), and the total PM within the second sample has been accurately predicted (e.g., by adding $M_{2-soot}$, $M_{2-SOF}$, and $M_{2-sulfate}$).

The computer 29 may be programmed to utilize the above formulae/algorithms in order to provide an accurate, differentiated indication of the total PM within a given exhaust sample, were it to be measured in a laboratory. Further, the computer 29 may be configured to output the composition of the PM (e.g., to the computer's monitor, or to a printable read-out, etc.) within any exhaust sample for each moment of the measurement period (e.g., respective amounts of soot, SOF, and sulfate within the exhaust sample).

Although an embodiment has been disclosed, a worker of ordinary skill in this art would recognize that certain modifications would come within the scope of this disclosure. For one, while a vehicle is shown, this disclosure can be used with a stand alone engine. Additionally, while electrical harnesses 30 are shown, the computer 29 may communicate with the various above-referenced devices wirelessly. Further, while this disclosure may be used to determine respective amounts of soot, SOF, and sulfate within an exhaust sample, one may utilize aspects of this disclosure separately (e.g., one could use this disclosure to determine the amount of SOF within an exhaust sample, without determining the amount of sulfate within that sample). For these reasons, the following claims should be studied to determine the true scope and content of this disclosure.

What is claimed is:

1. A system comprising:
    a sensor;
    a filter; and
    a computer including a processor, the computer programmed to identify at least one quantity of particulate matter within a first exhaust sample provided during a first period having a first duration based on at least one parameter associated with a second exhaust sample provided during a second period having a second duration that is different than the first duration.

2. The system of claim 1, wherein the at least one quantity includes an amount of sulfate within the first exhaust sample.

3. The system of claim 2, wherein the at least one parameter includes a sulfate-make factor determined based on an amount of sulfate within the second exhaust sample.

4. The system of claim 3, wherein the amount of sulfate within the second exhaust sample is collected on the filter.

5. The system of claim 1, wherein the at least one quantity includes an amount of SOF within the first exhaust sample.

6. The system of claim 5, wherein the amount of SOF is determined based in part on a measurement of the sensor, the measurement of the sensor indicative of an amount of soot within the first exhaust sample.

7. The system of claim 6, wherein the at least one parameter includes a proportionality factor determined, at least in part, based on amounts of SOF and soot within the second exhaust sample.

8. The system of claim 7, wherein the proportionality factor is further determined based on a measured concentration of hydrocarbon gasses within the second exhaust sample.

9. The system of claim 1, wherein the second duration is greater than the first duration.

10. The system of claim 1, wherein the second period includes the first period.

11. The system of claim 1, wherein the first period occurs outside of the second period.

12. The system of claim 1, wherein the first period occurs after the second period.

13. A method comprising the steps of:
   a) providing a first exhaust sample during a first period having a first duration; and
   b) determining at least one quantity of particulate matter within the first exhaust sample based on at least one identified parameter associated with a second exhaust sample provided during a second period having a second duration that is different than the first duration.

14. The method of claim 13, wherein the at least one identified parameter includes a proportionality factor, the proportionality factor determined by relating a ratio of SOF to soot identified in the second exhaust sample to a concentration of hydrocarbon gas within the second exhaust sample.

15. The method of claim 14, wherein the at least one identified parameter further includes a sulfate-make factor associated with a concentration of sulfate in the second exhaust sample.

16. The method of claim 15, wherein the at least one quantity includes amounts of SOF and sulfate within the first exhaust sample, and wherein the amount of SOF within the exhaust is determined based, at least in part, on the proportionality factor, and wherein the amount of sulfate within the first exhaust sample is determined based, at least in part, on the sulfate-make factor.

17. The method of claim 16, wherein the at least one quantity includes an amount of soot within the first exhaust sample.

18. The method of claim 17, wherein step b) is performed on board a vehicle.

19. The method of claim 16, wherein the first exhaust sample is provided during a portion of the second period during which the second exhaust sample is provided.

20. The method of claim 16, wherein the first exhaust sample is provided after the second exhaust sample.

21. The method of claim 13, wherein the second duration is greater than the first duration.

22. The method of claim 13, wherein the second period includes the first period.

23. The method of claim 13, wherein the first period occurs outside of the second period.

24. The method of claim 13, wherein the first period occurs after the second period.

* * * * *